United States Patent [19]

Yamanaka

[11] Patent Number: 4,608,258

[45] Date of Patent: Aug. 26, 1986

[54] MEDICAMENT FOR TREATMENT OF DIARRHEA

[75] Inventor: Kiyoyuki Yamanaka, Moriguchi, Japan

[73] Assignee: Taiko Pharmaceutical Co., Ltd., Suita, Japan

[21] Appl. No.: 523,885

[22] Filed: Aug. 17, 1983

[51] Int. Cl.⁴ ............................................. A61K 35/78
[52] U.S. Cl. ................................................. 424/195.1
[58] Field of Search ..................................... 424/195.1

[56] References Cited

U.S. PATENT DOCUMENTS 4,024,223   5/1977   Noda et al. ................... 424/180

OTHER PUBLICATIONS

Merck Index 9th ed., 1976, p. 334, No. 2568.

Handbook of Nonprescription Drugs, 6th ed., 1977, p. 100.

*Primary Examiner*—Albert T. Meyers
*Assistant Examiner*—John W. Rollins, Jr.
*Attorney, Agent, or Firm*—Armstrong, Nikaido, Marmelstein & Kubovcik

[57] ABSTRACT

Creosote has a novel pharmaceutical efficacy for treatment of various diseases with diarrhea. The medicament according to the present invention usually contains creosote, coptidis rhizoma, glycyrrhizae radix pulverata, cyperi rhizoma, auranti pericarpium and glycerinum, and it especially consists of 400 mg % of creosote, 200 mg % of coptidis rhizoma, 200 mg % of glycyrrhizae radix pulverata, 150 mg % of cyperi rhizoma, 200 mg % of auranti pericarpium and 100 mg % of glycerinum in each 9 pills.

1 Claim, No Drawings

MEDICAMENT FOR TREATMENT OF DIARRHEA

FIELD OF INVENTION

This invention relates to a novel usage of creosote as a medicament for treatment of diarrhea.

Creosote is a mixture of phenols and is obtained by the distillation of beechwood tar at about 200°–220°. Creosote consists of mainly phenol, cresol, guaiacol, xylenol and creosol. Creosote is a colorless or pale yellowish liquid and has a characteristic smoky odor and burning taste. This is hardly dissolved in water but is miscible with ethanol, ether, chloroform or soy-bean oil. Creosote has been recommended as a gastrointestinal antiseptic in the treatment of fermentative gastritis and enteritis and for its local anesthetic action upon the gastric mucosa in nausea and vomiting. And it has been also employed by dentists for obtunding sensitive dentine and as an ingredient of pastes for destruction of nerves. One or two drops of the pure substance are carefully introduced into the hollow of the tooth on a little cotton avoiding contact with the tongue or cheek.

However, it has never been known that creosote has other pharmaceutical efficacy than the above mentioned gastrointestinal antiseptic, etc.

SUMMARY OF INVENTION

Now we have found a novel pharmaceutical efficacy of creosote. Creosote has an outstanding pharmaceutical efficacy for treatment of various diseases with diarrhea, coupled with low toxicity.

Creosote is usally in form of pills, and pills may have sugar coat. And a medicament according to the present invention consists of creosote, coptidis rhizoma, glycyrrhizae radix pulverata, cyperi rhyzoma, auranti pericarpium and glycerinum.

DETAILED DESCRIPTION OF INVENTION

Acute toxicity tests of creosote in mice and rats are as follows:

(a) Test Material

Beechwood creosote used in the present tests was supplied by Perstorp Chemishe Werke (Perstorp, Sweden; lot. number 50623). A quantitative and qualitative analysis of this material by gaschromatography (Shimadzu, GC-4CMPE) is shown in TABLE 1.

TABLE 1

Analysis of the chemical components of beechwood creosote (Perstorp Chemische Werke, Lot. NO. 50623) by gas chromatography

|   | Components | % |
| --- | --- | --- |
| 1 | phenol | 12.84 |
| 2 | o-cresol | 8.69 |
| 3 | m-cresol | 11.71 |
|   | p-cresol |   |
| 4 | guaiacol | 23.48 |
| 5 | 2,6-xyloenol | 1.45 |
| 6 | 2,5-xylenol | 6.36 |
| 7 | 3,5-xylenol | 2.56 |
| 8 | creosol | 24.48 |
| 9 | unknown | 8.38 |
|   | Total | 99.95 |

(b) Experimental animals

Male and female ddY mice and Wistar rats were supplied from Shizuoka Agricultural Co. Assoc. for Laboratory Animals, and kept under observation for 1 week to establish their state of health. Powdered laboratory chaw (Oriental Yeast Co. Ltd., M) and water were available ad lib. The animals were randomly placed in wire-bottomed cages (3 mice and 2 or 3 rats per cage; CLEA Japan, CL-0206 and CL-239). Experiments were done in the isolated animal room which was automatically controlled under continuous ventilation and artificial lightening at 23±2° and 55±5% relative humidity.

(c) Method

Aqueous solution of creosote (10%, v/v) was prepared by emulsifying creosote in water containing 33% of polyethylene glycol 400. The toxicity of PEG 400 at this concentration was negligible as determined by the concurrent control experiment. Female and male mice, weighing 20±1 g in female and 21±2 g in male, and rats weighing 78±7 g in female and 98±10 g in male, in groups of 10 animals each, were deprived of food overnight, and creosote solution was then administered orally using a stomach tube. The dose levels of creosote in mice and rats are given in TABLE 2. All animals were kept under observation for 7 days after creosote administration to elucidate the symptoms of poisoning and mortality of the animals. Single oral $LD_{50}$ values were calculated by a formula of Litchfield-Wilconxon. The difference of mortality between female and male animals was compared statistically using Cochran's test.

TABLE 2

Acute toxicity of creosote after an oral administration in mice and rats

| Animal | Sex | Dose (mg/kg) | No. of animals examined | No. of dead animals | Number of animals died within | | | | |
| --- | --- | --- | --- | --- | --- | --- | --- | --- | --- |
|   |   |   |   |   | 30 min | 5 hr | 24 hr | 48 hr | 7 days |
| Mouse | F | 313 | 10 | 0 |   |   |   |   |   |
|   |   | 376 | 10 | 3 |   |   | 3 |   |   |
|   |   | 451 | 10 | 8 | 3 | 5 |   |   |   |
|   |   | 541 | 10 | 8 | 2 | 6 |   |   |   |
|   |   | 650 | 10 | 9 | 1 | 8 |   |   |   |
|   |   | 780 | 10 | 10 | 2 | 8 |   |   |   |
|   | M | 376 | 10 | 0 |   |   |   |   |   |
|   |   | 451 | 10 | 3 |   | 1 | 2 |   |   |
|   |   | 541 | 10 | 7 | 1 | 4 | 1 |   | 1 |
|   |   | 650 | 10 | 5 | 1 | 3 | 1 |   |   |
|   |   | 780 | 10 | 9 | 2 | 7 |   |   |   |
|   |   | 936 | 10 | 10 | 6 | 3 |   | 1 |   |
| Rat | F | 600 | 10 | 0 |   |   |   |   |   |
|   |   | 700 | 10 | 1 | 1 |   |   |   |   |
|   |   | 800 | 10 | 1 |   |   |   |   | 1 |
|   |   | 900 | 10 | 6 | 1 | 1 | 3 |   | 1 |
|   |   | 1000 | 10 | 9 | 1 | 1 | 7 |   |   |

TABLE 2-continued

Acute toxicity of creosote after an oral administration in mice and rats

| Animal | Sex | Dose (mg/kg) | No. of animals examined | No. of dead animals | 30 min | 5 hr | 24 hr | 48 hr | 7 days |
|---|---|---|---|---|---|---|---|---|---|
|  |  | 1100 | 10 | 10 | 5 | 1 | 4 |  |  |
|  | M | 600 |  | 0 |  |  |  |  |  |
|  |  | 700 | 10 | 1 | 1 |  |  |  |  |
|  |  | 800 | 10 | 2 |  |  | 2 |  |  |
|  |  | 900 | 10 | 6 | 1 | 2 | 3 |  |  |
|  |  | 1000 | 10 | 8 | 1 | 1 | 5 | 1 |  |
|  |  | 1100 | 10 | 10 | 2 |  | 8 |  |  |

TABLE 3

Oral $LD_{50}$ values of creosote in mice and rats

| Animal | Sex | $LD_{50}$ (mg/kg) | 95% confidence limit (mg/kg) |
|---|---|---|---|
| Mouse | F | 433 | 386–486 |
|  | M | 525 | 453–609 |
| Rat | F | 870 | 815–928 |
|  | M | 885 | 826–949 |

(d) Results

The results of acute toxicity to single oral administration of creosote are shown in TABLE 2 and single oral $LD_{50}$ values calculated from these data and 95% confidence limits of each value are shown in TABLE 3. The single oral $LD_{50}$ values in mice were 433 mg/kg in female and 525 mg/kg in male, and those in rats were 870 mg/kg in female and 885 mg/kg in male. The mortality of female mice was significantly higher than that of male mice, while there was no significant difference between the mortality of female and male rats (Cochran's test with $P<0.05$).

The first sign of poisoning noted in mice and rats to which higher concentrations of creosote has been administered was a twitching of the muscles followed by a convulsion. The first twitching occured almost invariably in the extrinsic eye muscles and those of the eyelids and ears, then spread to isolated muscle bundles all over the body. These animals usually showed a marked convulsion 1 or 2 minutes after administration. Then, convulsion diminished gradually, giving way to a state of asphyxia and coma. Pulse and respiration were increased in the rate at first, but later become slow, irregular and weak. Most of these animals died within 30 minutes. The remaining animals gradually recovered, but several weakened animals died within 1 week after administration. Symptons of poisoning produced by lower concentrations of creosote resembled those described above, but on the whole convulsion was less severe, animals recovered more rapidly, and asphyxia or coma were observed on a small number of animals.

"Creosote Capsule" was administered to patients with various diseases who complained of diarrhea and efficacy of this therapy was evaluated on the basis of improvement of subjective and objective symptoms.

This drug was markedly effective for the improvement of abdominal pain, abdominal fullness, stool condition and frequency of defecation. In the evaluation of general efficacy, some efficacy was noted in all of the 148 patients. Namely, this drug was evaluated as markedly effective in 44, effective in 71 and sightly effective in 13.

Moreover, this drug was effective, regardless of sexes. When relationship between the rate of efficacy and age was examined, efficacy of "creosote" was noted in all age groups, though it was slightly higher in the younger generation. When relationship between various diseases with diarrhea and efficacy of "creosote" was examined, this drug was effective for all the patients with simple or habitual diarrhea and irritable or nervous diarrhea and about 70–80% of the patients with enterogastritis or acute enteritis.

On the other hand, the efficacy of this drug tended to be lower in chronic diseases. Accordingly, it is suggested that "creosote" may be an effective drug of the first choice for the treatment of moderate or mild diarrheal symptons which accompany relatively mild diseases and hardly induce, as basal diseases, organic disorderes of the digestive system. This implies wide range of application of "creosote" to diarrheal symptoms.

As side effects, each one patient with mild heartburn, mild nausea (mere irritation sympton), abdominal fullness and general redness (treatment was discontinued because of increased itching on the 2nd day) were noted (4 in total). However, since all of these symptons were mild and disappeared after short duration without any special treatment or discontinuance of medication, these were not regarded as definite adverse effects of this drug.

As described above, "creosote" has long been used by many people and it has been known to have high efficacy and usefulness and low incidence of adverse effects. On the basis of dosage and duration of treatment used in this study, it is expected that "creosote" may exert efficacy without any noticeable adverse effects.

Clinical trial with creosote in various diseases with diarrhea is as follows:

(a) Materials and Methods (1) Patients and Diseases

This clinical trial was performed on the patients who were evaluated to be fitted for this purpose by their physicians on the basis of various laboratory data and other findings obtained during first visit.

(2) Age and Sex

The subjects of this study consisted of both male and female patients aged 15 to 85 years.

(3) Test material

Since single-taste oral administration of the test material was difficult because of its specific odor and taste, it was administered in a form of capsules with a vehicle (absorbent) to ensure accurate dosage.

| Drug form | Contents of the constituents/capsule | |
|---|---|---|
| Capsule | J.P. Creosote | 166 mg |
|  | Metasilicic magnesium aluminate | 66 mg |
| Dosage | | |
| 3 Capsules/day (t.i.d) after each meal | | |
| Duration of treatment | | |
| 3 days as a rule | | |

During treatment with the test material, administration of other drugs such as creosote preparations, berbelic agents, antibiotics, synthetic antibacterials and intestinal drugs was avoided, if possible.

(a) Names of disease and No. of patients

| Diagnosis | No. of patients | Diagnosis | No. of patients |
|---|---|---|---|
| Acute enteritis | 71 | Nervous diarrhea | 3 |
| Acute enterogastritis | 7 | Enterogastritis | 3 |
| Acute colitis | 6 | Nervous enterogastritis | 1 |
| Chronic enterogastritis | 2 | Ulcerative colitis | 3 |
| Chronic enteritis | 6 | Habitual diarrhea | 1 |
| Chronic colitis | 1 | Catarrhal colitis | 1 |
| Chronic diarrhea | 1 | Colitis | 3 |
| Enterogastritis due to cold | 14 | Hemorrhagic gastriti | 1 |
| Simple diarrhea | 12 | Gastric ulcer | 1 |
| Irritable colitis | 5 | Acute pancreatitis | 1 |
| Gastrogenic diarrhea | 3 | Suspected food poisoning | 2 |
| Subtotal | | Total | |

(b) No. of patients of sexes
Male: 71
Female: 77

(c) Age distribution

| Age (years) | No. of patients |
|---|---|
| 20 or younger | 6 |
| 21–30 | 30 |
| 31–40 | 23 |
| 41–50 | 22 |
| 51–60 | 31 |
| 61 or older | 36 |
| Total | 148 |

(d) Clinical course

Clinical course was observed for condition of stool, frequncy of defecation, abdominal pain, abdominal fullness, nausea, loss of strength, headache, dry mouth and body temperature.

(e) Clinical rating scale

Markedly effective: The patient feels fine because diarrhea has disappeared and the condition of stool improved markedly within 3 days of treatment.

Effective: The patient can live a daily life without significant difficulty because diarrhea and the condition of stool have improved and various other symptoms have been ameliorated to a large extent within 3 days of treatment. Slightly effective: Diarrhea, stool condition and various other symptons have been ameliorated slightly as compared with those before treatment within 3 days of treatment.

No Change: No improvement can be noted even after 4 days of treatment.

(b) Results (1) Results of evaluation of general efficacy

When the effect of "creosote" on the patients with diarrhea was evaluated, the results were as shown in the following Table 4.

TABLE 4

| Results of evaluation of general efficacy | | |
|---|---|---|
| No. and Rate | No. | Rate (%) |
| Efficacy | | |
| Markedly effective (++) | 44 | 29.73 |
| Effective (+) | 72 | 48.65 |
| Slightly effective (±) | 13 | 8.78 |
| No change (−) | 19 | 12.84 |
| Total | 148 | 100.00 |

(2) Relationship between appearance of efficacy and sexes

When the presence of specific sex difference was examined in the improvement of diarrhea by the administration of "creosote", the results were as shown in Table 5. It is apparent from these table and figure that there is no specific sex difference in the improvement of diarrhea by "creosote".

TABLE 5

| Relationship between appearance of efficacy and sexes | | | | |
|---|---|---|---|---|
| | Male | | Female | |
| Sex, No. Rate | No. | Rate (%) | No. | Rate (%) |
| Markedly effective (++) | 21 | 29.58 | 23 | 29.87 |
| Effective (+) | 32 | 45.07 | 40 | 51.95 |
| Slightly effective (±) | 7 | 9.86 | 6 | 7.79 |
| No change (−) | 11 | 15.49 | 8 | 10.39 |
| Total | 71 | 100.00 | 77 | 100.00 |

(3) Relationship between appearance and ages

Table 6 shows relationship between appearance of efficacy of "creosote" and ages.

According to this table, the rate of efficacy was highest in the age group of 21 30 years and no significant difference was noted among age groups other than the youngest one (20 or less). On the other hand, the rate of no change was highest (31.25%) in the group of 60 or more years and lowest in the group of 21 to 30 years, suggesting decrease in the rate of no change with decrease in age.

The rate of efficacy described above means the percentage of patients for whom this therapy was markedly effective or effective, and the rate of no change, the percentage of patients for whom it was slightly effective or uneffective.

TABLE 6

| Relationship between appearance of efficacy and ages | | | | | | | | |
|---|---|---|---|---|---|---|---|---|
| Degrees and rates of efficacy | Markedly effective | | Effective | | Slightly effective | | No change | |
| Age (years) | No. | % | No. | % | No. | % | No. | % |
| 20 or less | 2 | 4.44 | 4 | 5.63 | 0 | 0 | 2 | 10.53 |
| 21–30 | 12 | 26.67 | 15 | 21.13 | 0 | 0 | 3 | 15.79 |
| 31–40 | 9 | 20.00 | 11 | 15.49 | 2 | 15.38 | 3 | 15.79 |
| 41–50 | 6 | 13.33 | 12 | 16.90 | 0 | 0 | 5 | 26.32 |
| 51–60 | 7 | 15.56 | 16 | 22.54 | 5 | 38.46 | 2 | 10.53 |
| 61 or more | 9 | 20.00 | 13 | 18.31 | 6 | 46.15 | 4 | 21.05 |
| Total | 45 | 100.00 | 71 | 100.00 | 13 | 99.99 | 19 | 100.01 |

(4) Various diseases and appearance of efficacy

Table 7 shows relationship between various diseases with diarrhea studied and appearance of efficacy of "creosote" therapy. This table suggests that the rate of efficacy is high in acute enteritis, simple and habitual diarrhea, enterogastritis due to cold and enterogastritis and irritable and nervous diarrhea.

and general redness (treatment was discontinued on the 2nd day of treatment because of increased itching) were noted (4 in total). These symptoms were mild and disappeared without any special treatment or discontinuance of administration in all but one.

TABLE 5

| Evaluation (%) Diagnosis | Efficacy on diarrhea in various diseases | | | | | | | | No. of patients |
|---|---|---|---|---|---|---|---|---|---|
| | Markedly effective (++) | | Effective (+) | | Slightly effective (+) | | No change (−) | | |
| | No. | % | No. | % | No. | % | No. | % | |
| Acute enteritis | 25 | 35.21 | 30 | 45.25 | 8 | 11.27 | 8 | 11.27 | 71 |
| Acute enterogastritis | 1 | 14.29 | 5 | 71.43 | 0 | 0 | 1 | 14.29 | 7 |
| Acute colitis | 1 | 16.67 | 5 | 83.33 | 0 | 0 | 0 | 0 | 6 |
| Chronic enteritis | 0 | 0 | 3 | 50.00 | 2 | 33.33 | 1 | 16.67 | 6 |
| Chronic Enterogastritis | 0 | 0 | 0 | 0 | 1 | 50.00 | 1 | 50.00 | 2 |
| Chronic colitis | 0 | 0 | 0 | 0 | 0 | 0 | 1 | 100.00 | 1 |
| Chronic diarrhea | 0 | 0 | 1 | 100.00 | 0 | 0 | 0 | 0 | 1 |
| Enterogastritis due to cold | 2 | 14.29 | 10 | 71.43 | 1 | 7.14 | 1 | 7.14 | 14 |
| Simple diarrhea | 9 | 75.00 | 3 | 25.00 | 0 | 0 | 0 | 0 | 12 |
| Irritable colitis | 3 | 60.00 | 2 | 40.00 | 0 | 0 | 0 | 0 | 5 |
| Gastrogenic diarrhea | 0 | 0 | 3 | 100.00 | 0 | 0 | 0 | 0 | 3 |
| Nervous diarrhea | 2 | 66.67 | 1 | 33.33 | 0 | 0 | 0 | 0 | 3 |
| Enterogastritis | 1 | 33.33 | 1 | 33.33 | 0 | 0 | 1 | 33.33 | 3 |
| Nervous enterogastritis | 0 | 0 | 1 | 100.00 | 0 | 0 | 0 | 0 | 1 |
| Ulcerative colitis | 0 | 0 | 2 | 66.67 | 0 | 0 | 1 | 33.33 | 3 |
| Habitual diarrhea | 0 | 0 | 1 | 100.00 | 0 | 0 | 0 | 0 | 1 |
| Catarrhal colitis | 0 | 0 | 1 | 100.00 | 0 | 0 | 0 | 0 | 1 |
| Colitis | 0 | 0 | 1 | 33.33 | 0 | 0 | 2 | 66.67 | 3 |
| Hemorrhagic gastritis | 0 | 0 | 0 | 0 | 0 | 0 | 1 | 100.00 | 1 |
| Gastric ulcer | 0 | 0 | 0 | 0 | 1 | 100.00 | 0 | 0 | 1 |
| Acute pancreatitis | 0 | 0 | 1 | 100.00 | 0 | 0 | 0 | 0 | 1 |
| Suspected food poisoning | 0 | 0 | 1 | 50.00 | 0 | 0 | 1 | 50.00 | 2 |
| Total | 44 | | 72 | | 13 | | 19 | | 148 |

(5) Drug administration and improvement of defecating frequency and stool condition Administration of "creosote" resulted in the improvement of defecting frequency per day in the patients for whom this therapy was evaluated as markedly effective, effective or slightly effective. In addition, improvement of stool from mucus or watery to caddy, soft or normal was noted in all the patients for whom this therapy was evaluated as effective (markedly effective+effective) and in almost all the patients for whom it was evaluated as slightly effective.

(6) Side effects

As adverse effects probably due to this drug, each 1 case of abdominal fullness, mild nausea, mild heartburn

EXAMPLE

A medicament consists of 400 mg% of creosote, 200 mg% of coptidis rhizoma, 200 mg% of glycyrrhizae radix pulverata, 150 mg% of cyperi rhizoma, 200 mg% of auranti pericarpium and 100 mg% of glycerinum in each 9 pills.

What is claimed is:

1. A diarrhea-treating medicament for treating various diseases with diarrhea comprising a diarrhea-treating effective amount of creosote and a pharamceutically acceptable carrier, wherein the medicament is contained in a capsule.

* * * * *